United States Patent [19]

Schroeck

[11] 3,937,721

[45] Feb. 10, 1976

[54] METHOD FOR THE PREPARATION OF SULFONIC ACID ESTERS FROM FREE SULFONIC ACIDS

[75] Inventor: Calvin William Schroeck, Eastlake, Ohio

[73] Assignee: The Lubrizol Corporation, Cleveland, Ohio

[22] Filed: May 9, 1974

[21] Appl. No.: 468,359

Related U.S. Application Data

[62] Division of Ser. No. 358,213, May 7, 1973.

[52] U.S. Cl. ...... 260/456 A; 260/456 R; 260/456 P; 260/983

[51] Int. Cl.$^2$ ...................................... C07C 143/16

[58] Field of Search ........ 260/456 R, 456 P, 456 A, 260/983, 456

[56] References Cited

UNITED STATES PATENTS

| | | | |
|---|---|---|---|
| 1,321,994 | 11/1919 | Downs | 260/505 E |
| 1,422,564 | 7/1922 | Grob et al. | 260/505 E |
| 2,268,443 | 12/1941 | Crowder | 260/505 E |
| 2,674,616 | 4/1954 | Morris | 260/983 X |
| 3,160,632 | 12/1964 | Toy et al. | 260/268 |
| 3,206,492 | 9/1965 | Turbak et al. | 260/456 P |
| 3,600,470 | 8/1971 | Lewis | 260/924 |

FOREIGN PATENTS OR APPLICATIONS

756,099   8/1956   United Kingdom ............ 260/456 R

OTHER PUBLICATIONS

Gilbert, "Sulfonation and Related Reactions," pp. 15–16 (1965).

Hoffmann et al., J. Amer. Chem. Soc., 79, 4759 (1957).

*Primary Examiner*—James O. Thomas, Jr.
*Assistant Examiner*—Nicky Chan
*Attorney, Agent, or Firm*—James W. Adams, Jr.; William H. Pittman

[57] ABSTRACT

Sulfonic acids, particularly amido-substituted sulfonic acids and preferably acrylamidoalkanesulfonic acids, can be esterified by reaction with (A) an ester of phosphoric acid or (B) an adduct of an ester of a strong acid (preferably sulfuric acid) with an amide such as dimethylformamide. This method is especially useful for the preparation of lower alkyl esters, especially the methyl and ethyl esters. The esters are useful monomers, especially for copolymerization with acrylic compounds to produce polymers of improved dyeability.

4 Claims, No Drawings

METHOD FOR THE PREPARATION OF SULFONIC ACID ESTERS FROM FREE SULFONIC ACIDS

This is a division of application Ser. No. 358,213 filed May 7, 1973.

This invention relates to new methods for preparing compositions of matter, and particularly for preparing sulfonic acid esters. Still more particularly, it relates to a method for the preparation of a sulfonic acid ester which comprises reacting the corresponding sulfonic acid with a compound having one of the formulas

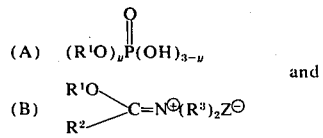

wherein:
$R^1$ is a monovalent aliphatic, cycloaliphatic or arylaliphatic radical or a corresponding substituted radical;
each of $R^2$ and $R^3$ is hydrogen or a hydrocarbon or substituted hydrocarbon radical;
$Z^\ominus$ is an anion; and
$y$ is 1, 2 or 3.

The preparation of sulfonic acid esters, especially the alkyl esters, cannot ordinarily be effected by convenient means from the free sulfonic acid. The most usual method for the preparation of these compounds is to convert the acid to the sulfonyl chloride and to react said sulfonyl chloride with an alcohol. This method is cumbersome since it involves two steps, and somewhat hazardous since the reagents used to convert the acid to its chloride are toxic and difficult to handle. Likewise, direct esterification reagents such as diazomethane are not entirely safe.

A principal object of this invention, therefore, is to provide a new method for the preparation of sulfonic acid esters.

A further object is to provide a convenient onestep method for preparing esters of sulfonic acids in high yield.

Still another object is to provide a method for sulfonic acid ester preparation which does not involve the use of dangerous reagents.

A further object is to prepare esters of unsaturated sulfonic acids, and particularly acrylamidoalkanesulfonic acids.

Other objects will in part be obvious and will in part appear hereinafter.

Any sulfonic acid may be esterified by the method of this invention. Thus, suitable acids include aliphatic ones such as methanesulfonic acid, ethanesulfonic acid, 2-propanesulfonic acid and the like; aromatic acids such as benzenesulfonic acid, p-toluenesulfonic acid, 2-napthalenesulfonic acid and the like; heterocyclic sulfonic acids such as 3-pyridinesulfonic acid; amido-substituted sulfonic acids such as 2-acetamidopropanesulfonic acid, 2-acrylamidopropanesulfonic acid, 2-acrylamido-2-methylpropanesulfonic acid, 4-acrylamidobenzenesulfonic acid and the like. The particularly preferred acids, for the purpose of this invention, are those containing aliphatic olefinic bonds and especially simple olefinic sulfonic acids and acrylamidoalkanesulfonic acids, such as 2-methyl-2-propenesulfonic acid and 2-acrylamido-2-methylpropanesulfonic acid.

As previously indicated, the method of this invention involves the use of an esterification reagent having one of two structures, hereinafter sometimes referred to as reagent A and reagent B. Reagent A is an aliphatic, cycloaliphatic or arylaliphatic ester of phosphoric acid and may be a monoester, diester, triester or mixture of two or more of such esters, but the triesters (those in which $y$ is 3) are preferred. In such phosphoric acid esters, $R^1$ may be aliphatic, cycloaliphatic or arylaliphatic or a substituted derivative of any of these. By "substituted" is meant radicals containing substituents which do not alter significantly their character or reactivity. Examples are:

Halide (fluoride, chloride, bromide, iodide)
Hydroxy
Ether (especially lower alkoxy wherein "lower" denotes radicals containing up to seven carbon atoms)
Keto
Carboxy
Ester (especially lower carbalkoxy)
Aminoacyl (amide)
Nitro
Cyano
Thioether
Sulfoxy
Sulfone
Sulfonic acid (and derivatives thereof)

In general, no more than three such substituent groups will be present for each 10 carbon atoms in the radical.

In the preferred compounds used as reagent A, $R^1$ will be a lower alkyl radical, especially methyl or ethyl.

Reagent B which may also be used in the method of this invention is a quaternary imidate which may be prepared by the reaction of a suitable amide with an ester of a strong acid. In reagent B, $R^1$ is as previously defined. Each of $R^2$ and $R^3$ is hydrogen or a hydrocarbon or substituted hydrocarbon radical; the term "hydrocarbon radical" as used herein includes aliphatic, cycloaliphatic and aromatic (including aliphatic- and cycloaliphatic-substituted aromatic and aromatic-substituted aliphatic and cycloaliphatic) radicals. It also includes cyclic radicals wherein the ring is completed through another portion of the molecule; that is, any two indicated substituents may together form a cycloalkyl radical.

The following are illustrative of hydrocarbon radicals within the scope of this invention. Where a named radical has several isomeric forms (e.g., butyl), all such forms are included.

| | |
|---|---|
| Methyl | Benzyl |
| Ethyl | Cyclohexyl |
| Propyl | Cyclopentyl |
| Butyl | Methylcyclopentyl |
| Hexyl | Cyclopentadienyl |
| Octyl | Vinylphenyl |
| Decyl | Isopropenylphenyl |
| Vinyl | Cinnamyl |
| Allyl | Naphthyl |
| Ethynyl | |
| Propargyl | |
| Phenyl | |
| Tolyl | |
| Xylyl | |

—$C_6H_3(C_2H_5)_2$
—$C_6H_4(CH_2)_{11}CH_3$

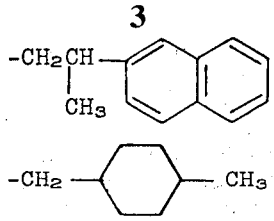

Many obvious variations of these radicals will be apparent to those skilled in the art and are included within the scope of the invention.

Substituted hydrocarbon, alkyl, aryl, etc., radicals (the word "substituted" being defined hereinabove) are considered fully equivalent to the hydrocarbon, alkyl, aryl, etc., radicals and to be part of this invention.

Preferably, the hydrocarbon or substituted hydrocarbon radicals in reagent B are free from ethylenic and acetylenic unsaturation and have no more than about 30 carbon atoms, desirably no more than about 12 carbon atoms. A particular preference is expressed for compounds in which $R^2$ is hydrogen and $R^3$ is a lower alkyl radical, the word "lower" being defined hereinabove. Still more preferably, $R^3$ is methyl.

The anion $Z^\ominus$ is derived from the strong acid ester previously mentioned. Thus, when the ester is a dialkyl sulfate $Z^\ominus$ is the monoalkyl sulfate anion.

A reagent particularly useful as reagent B can be prepared by the reaction of dimethyl sulfate with dimethylformamide in approximately equimolar amounts, as described in the examples hereinafter. This reaction is known in the art and is described, for example, in German Pat. No. 1,156,779.

The reaction between the sulfonic acid (or a salt thereof which is frequently equivalent to the free acid for the purposes of this invention) and reagent A or B is most conveniently effected at a temperature of about 50°–200°C., preferably about 70°–150°C. In general, a somewhat higher temperature is employed with reagent A than with reagent B. The reaction may be carried out in a suitable diluent such as acetone, ethylene glycol monomethyl ether, benzene, toluene, dimethylformamide, dimethyl sulfoxide or the like. The proportions of reagents used are not critical, although it is preferred to use at least one mole of reagent A or B per mole of sulfonic acid in order to convert as much sulfonic acid as possible to the desired ester. Generally, an excess of reagent A or B (typically about a twofold to fourfold excess) is used.

Following the completion of the esterification reaction, the desired ester may be recovered and purified by typical methods known in the art.

The method of this invention is illustrated by the following examples. All parts are by weight unless otherwise indicated.

EXAMPLE 1

A mixture of 41.4 parts (0.2 mole) of 2-acrylamido-2-methylpropanesulfonic acid, 73 parts (0.4 mole) of triethyl phosphate and 0.2 part of p-methoxyphenol (a polymerization and oxidation inhibitor) is heated to 120°–135°C. for 1¾ hours, with stirring. After 40 minutes, the slurry becomes homogeneous. Unreacted triethyl phosphate is removed under vacuum at 90°C., and during the removal 0.1 part of "Irganox 1010" (another inhibitor) is added. The residue is washed twice with hexane and dissolved in benzene; the benzene solution is washed with a saturated sodium sulfate solution, dried over magnesium sulfate and evaporated. The solid product is recrystallized from a benzene-hexane mixture. The hexane washings are diluted with methylene chloride and the solution is used to extract the aqueous sodium sulfate washings, dried over magnesium sulfate and evaporated. The combined crystalline product is the desired ethyl 2-acrylamido-2-methylpropanesulfonate and melts at 65°–67°C. The yield is 28.1 parts, or 60% of theoretical.

EXAMPLE 2

Following a procedure similar to that of Example 1, ethyl 2-methyl-2-propenesulfonate is prepared by the reaction of 2-methyl-2-propenesulfonic acid with triethyl phosphate.

EXAMPLE 3

A mixture of 63 grams (0.5 mole) of dimethyl sulfate and 37 grams (0.5 mole) of dimethylformamide is heated at 60°–80°C. for 3 hours. There are then added 52 grams (0.25 mole) of 2-acrylamido-2-methylpropanesulfonic acid, 700 ml. of benzene and 0.3 gram each of p-methoxyphenol, t-butylcatechol and 2,6-di-t-butylcresol. The mixture is heated under reflux, with stirring, for 24 hours and then most of the benzene is removed by distillation. Refluxing at 78°–80°C. is continued for 24 hours, after which the mixture is cooled and poured into 300 grams of ice water, and an additional 300 ml. of benzene is added. The organic and aqueous phases are separated and the aqueous phase is extracted with chloroform. The combined organic layers are dried over magnesium sulfate and the solvents are stripped. The desired methyl 2-acrylamido2-methylpropanesulfonate is recrystallized from toluene; after recrystallization, it melts at 77°–80°C.

EXAMPLE 4

An addition product of dimethyl sulfate and dimethylformamide is prepared according to the method of Example 3. To 0.5 mole of this product is added a mixture of 59 grams (0.25 mole) of sodium 2-acrylamido-2-methylpropanesulfonate, 0.1 gram of p-methoxyphenol and 500 ml. of benzene. The mixture is heated under reflux, with stirring, for 3 hours, after which the benzene is evaporated under vacuum. The remaining solid is recrystallized from a benzene-cyclohexane mixture to yield the desired methyl 2-acrylamido-2-methylpropanesulfonate.

EXAMPLE 5

Following a procedure similar to that of Example 4, methyl-p-toluenesulfonate is prepared by the reaction of 0.5 mole of p-toluenesulfonic acid with one mole of the dimethyl sulfate-dimethylformamide reaction product.

Sulfonic acid esters, as a class, may be used as latent sources of the corresponding sulfonic acids (e.g., by reaction with an alcohol) and as alkylating agents.

Esters of polymerizable sulfonic acids, such as methyl 2-methyl-2-propenesulfonate and methyl 2-acrylamido-2-methylpropanesulfonate, may be polymerized under freeradical conditions, either alone or in the presence of other monomers. The term "polymer," as used herein, includes addition homopolymers, copolymers, terpolymers and other interpolymers.

Polymerization by the free-radical method may be effected in bulk, solution, suspension or emulsion, by contacting the monomer or monomers with a polymerization initiator either in the absence or presence of a diluent at a temperature of about 0°–200°C. Suitable initiators include benzoyl peroxide, tertiary butyl hydroperoxide, acetyl peroxide, hydrogen peroxide, azobisisobutyronitrile, persulfate-bisulfite, persulfate-sodium formaldehyde sulfoxylate, chlorate-sulfite and the like.

A large variety of polymerizable compounds can be used to form interpolymers with sulfonic acid esters. They include (1) unsaturated monohydric alcohols and esters thereof, (2) unsaturated acids and esters thereof, (3) unsaturated polyhydric alcohols and esters thereof, (4) vinyl cyclic compounds, (5) unsaturated ethers, (6) unsaturated ketones, (7) unsaturated amides, (8) unsaturated aliphatic hydrocarbons, (9) unsaturated alkyl halides, (10) unsaturated acid anhydrides, (11) unsaturated acid chlorides, and (12) unsaturated nitriles. Specific illustrations of such compounds are:

1. Unsaturated alcohols and esters thereof: Allyl, methallyl, crotyl, 1-chloroallyl, 2-chloroallyl, cinnamyl, vinyl, methylvinyl, 1-phenallyl, butenyl alcohols, and esters of such alcohols with saturated acids such as acetic, propionic, butyric, valeric, caproic and stearic; with unsaturated acids such as acrylic, alpha-substituted acrylic (including alkylacrylic, e.g., methacrylic, ethylacrylic, propylacrylic, etc., and arylacrylic such as phenylacrylic), crotonic, oleic, linoleic and linolenic; with polybasic acids such as oxalic, malonic, succinic, glutaric, adipic, pimelic, suberic, azelaic and sebacic; with unsaturated polybasic acids such as maleic, fumaric, citraconic, mesaconic, itaconic, methylenemalonic, acetylenedicarboxylic and aconitic; and with aromatic acids, e.g., benzoic, phenylacetic, phthalic, terephthalic and benzoylphthalic acids.

2. Unsaturated acids (examples of which appear above) and esters thereof with saturated alcohols, such as methyl, ethyl, propyl, isopropyl, butyl, isobutyl, sec-butyl, tert-butyl, 2-ethylhexyl, cyclohexyl or behenyl alcohols.

3. Unsaturated polyhydric alcohols, e.g., butenediol, and esters thereof with saturated and unsaturated aliphatic and aromatic, monobasic and polybasic acids, examples of which appear above.

4. Vinyl cyclic compounds including styrene, o-, m-, p-chlorostyrenes, bromostyrenes, fluorostyrenes, methylstyrenes, ethylstryrenes and cyanostyrenes; di-, tri-, and tetra-chlorostyrenes, bromostyrenes, fluorostyrenes, methylstyrenes, ethylstyrenes, cyanostyrenes; vinylnaphthalene, vinylcyclohexane, divinylbenzene, trivinylbenzene, allylbenzene, and heterocycles such as vinylfuran, vinylpyridine, vinylbenzofuran, N-vinylcarbazole, N-vinylpyrrolidone and N-vinyloxazolidone.

5. Unsaturated ethers such as methyl vinyl ether, ethyl vinyl ether, cyclohexyl vinyl ether, octyl vinyl ether, diallyl ether, ethyl methallyl ether and allyl ethyl ether.

6. Unsaturated ketones, e.g., methyl vinyl ketone and ethyl vinyl ketone.

7. Unsaturated amides, such as acrylamide, methacrylamide, N-methylacrylamide, N-phenylacrylamide, N-allylacrylamide, N-methylolacrylamide, N-allylcaprolactam, diacetone acrylamide and hydroxymethylated diacetone acrylamide.

8. Unsaturated aliphatic hydrocarbons, for instance, ethylene, propylene, butenes, butadiene, isoprene, 2-chlorobutadiene and alpha-olefins in general.

9. Unsaturated alkyl halides, e.g., vinyl fluoride, vinyl chloride, vinyl bromide, vinylidene chloride, vinylidene bromide, allyl chloride and allyl bromide.

10. Unsaturated acid anhydrides, e.g., maleic, citraconic, itaconic, cis-4-cyclohexene-1,2-dicarboxylic and bicyclo(2,2,1)-5-heptene-2,3-dicarboxylic anhydrides.

11. Unsaturated acid halides such as cinnamoyl, acrylyl, methacrylyl, crotonyl, oleyl and fumaryl chlorides or bromides.

12. Unsaturated nitriles, e.g., acrylonitrile, methacrylonitrile and other substituted acrylonitriles.

The especially preferred polymers are the copolymers with acrylic monomers; that is, with acids such as acrylic and methacrylic acids and their esters, amides and nitriles. Copolymers with acrylonitrile are especially useful for the preparation of textile fibers because of their affinity for dyes.

The preparation of polymers of polymerizable sulfonic acid esters is illustrated by the following examples.

EXAMPLE 6

A resin flask is charged with 100 ml. of a 0.0008 N sulfuric acid solution, flushed with nitrogen and heated to 50°C. There are then added simultaneously, with stirring, the following: (1) a mixture of 100 grams of acrylonitrile and 3.4 grams of methyl 2-acrylamido-2-methylpropanesulfonate, (2) a solution of 0.75 part of potassium persulfate in 100 ml. of water, (3) a solution of 2.1 parts of sodium metabisulfite in 100 ml. of water, and (4) 100 ml. of a 0.0024 N solution of sulfuric acid. The addition time for the four solutions is 55 minutes. After addition is complete, the flask is cooled in ice water and the contents are poured into 3 liters of water. The desired copolymer precipitates and is washed with water and dried in a vacuum oven at 70°C. It is found to have excellent incorporation of Sevron Blue 2G dye.

EXAMPLE 7

Following substantially the procedure of Example 6, a copolymer is prepared from 100 parts of acrylonitrile and 3.4 parts of methyl 2-methyl-2-propenesulfonate.

EXAMPLE 8

A mixture of 47.5 parts of styrene, 2.5 parts of methyl 2-acrylamido-2-methylpropanesulfonate and 0.1 part of azobisisobutyronitrile is heated overnight at 100°C., under nitrogen. During this time, the mixture solidifies. It is dissolved in benzene and reprecipitated by pouring into methanol. The precipitate is then filtered, washed with methanol and dried; it is the desired copolymer.

EXAMPLE 9

A mixture of 209.9 parts of isodecyl acrylate, 11.05 parts of methyl 2-acrylamido-2-methylpropanesulfonate and 331 parts of heptane is heated to 60°C. under nitrogen, with stirring. Azobisisobutyronitrile, 0.44 part, is then added and stirring is continued at 60°C. for 20 hours, yielding a heptane solution of the desired copolymer.

What is claimed is:

1. A method for the preparation of a sulfonic acid ester which comprises reacting an acrylamidoalkanesulfonic acid with a compound having the formula

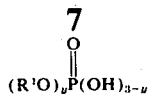
wherein
R¹ is a lower alkyl radical; and
y is 1, 2 or 3.
2. A method according to claim 1 wherein $y$ is 3.
3. A method according to claim 2 wherein the acrylamidoalkanesulfonic acid is 2-acrylamido-2-methylpropanesulfonic acid.
4. A method according to claim 3 wherein R¹ is methyl or ethyl.
* * * * *